United States Patent [19]
Peterson et al.

[11] Patent Number: 5,846,828
[45] Date of Patent: Dec. 8, 1998

[54] APPARATUS AND METHOD FOR STERILIZING, SEEDING, CULTURING, STORING, SHIPPING, AND TESTING TISSUE, SYNTHETIC, OR MECHANICAL HEART VALVES OR VALVE SEGMENTS

[75] Inventors: Alvin Peterson, Jamul; Lee K. Landeen, San Diego; John Bennett, San Diego; Jason Gee, San Diego, all of Calif.; Scott Chesla, Atlanta, Ga.; Joan Zeltinger, San Diego, Calif.

[73] Assignee: Advanced Tissue Sciences, La Jolla, Calif.

[21] Appl. No.: 478,309

[22] Filed: Jun. 7, 1995

[51] Int. Cl.⁶ .................................................. C12N 5/00
[52] U.S. Cl. .................. 435/399; 435/284.1; 435/286.5; 435/289.1; 623/2
[58] Field of Search ................................ 435/1.1, 284.1, 435/286.5, 286.6, 289.1, 293.1, 293.2, 297.2, 297.4, 303.1, 1.2, 395, 398, 399, 401, 402; 600/36; 623/1, 2

[56] References Cited

U.S. PATENT DOCUMENTS

| | | |
|---|---|---|
| 3,734,851 | 5/1973 | Matsumura . |
| 3,966,401 | 6/1976 | Hancock et al. . |
| 4,372,743 | 2/1983 | Lane . |
| 4,417,861 | 11/1983 | Tolbert . |
| 4,546,642 | 10/1985 | Swanson . |
| 4,639,422 | 1/1987 | Geimer et al. . |
| 4,839,280 | 6/1989 | Banes . |
| 4,988,623 | 1/1991 | Schwarz et al. . |
| 5,026,650 | 6/1991 | Schwarz et al. . |
| 5,043,260 | 8/1991 | Jauregul . |
| 5,081,035 | 1/1992 | Halberstadt et al. . |
| 5,153,131 | 10/1992 | Wolf et al. . |
| 5,153,132 | 10/1992 | Goodwin et al. . |
| 5,153,133 | 10/1992 | Schwarz et al. . |
| 5,155,034 | 10/1992 | Wolf et al. . |
| 5,155,035 | 10/1992 | Schwarz et al. . |
| 5,176,153 | 1/1993 | Eberhardt ..................................... 623/2 |
| 5,230,693 | 7/1993 | Williams et al. . |
| 5,266,480 | 11/1993 | Naughton et al. . |
| 5,272,909 | 12/1993 | Nguyen et al. . |
| 5,279,612 | 1/1994 | Eberhardt . |
| 5,308,764 | 5/1994 | Goodwin et al. . |
| 5,662,705 | 9/1997 | Love et al. ..................................... 623/2 |

FOREIGN PATENT DOCUMENTS

| | | |
|---|---|---|
| WO 90/13639 | 11/1990 | WIPO . |
| WO 92/11355 | 7/1992 | WIPO . |
| WO 93/01843 | 2/1993 | WIPO . |
| WO 93/12805 | 7/1993 | WIPO . |
| WO 93/18132 | 9/1993 | WIPO . |
| WO 94/25584 | 11/1994 | WIPO . |

OTHER PUBLICATIONS

Bengtsson et al. "Endothelialization of Mechanical Heart Valves." *J. Heart Valve Dis.* vol. 2(May 1993), pp. 352–355.
Eskin et al. "Behavior of Endothelial Cell Cultured on Silatic . . . " *Art. Organs.* vol. 7 (1983), pp. 31–37.
Schima et al. "Mechanical Simulation of Shear Stress . . . " *J. Biomech.* vol. 23 (1990), pp. 845–851.
Atkinson et al.; *Biochemical Engineering and Biotechnology Handbook;* pp. 476–487 (1991).
Halberstadt et al., "The In Vitro Growth of a Three–Dimensional Human Dermal Replacement Using a Single–Pass Perfusion System," *Biotechnology and Bioengineering* 43:740–746 (1994).

Primary Examiner—William H. Beisner
Attorney, Agent, or Firm—Pennie & Edmonds LLP

[57] ABSTRACT

An apparatus and method for sterilizing, seeding, culturing, storing, shipping, and testing heart valves is disclosed. Specifically, the present invention relates to an apparatus and method for dynamically seeding and culturing heart valves with human cells, resulting in a heart valve populated with viable human cells. In a preferred embodiment, the apparatus includes a fluid reservoir, a pneumatic pressure chamber, a pressure source for providing a varying pressure to the pressure chamber, and a heart valve holder. In an alternative exemplary embodiment, the apparatus includes a fluid reservoir, a pump, a venturi tube, a heart valve chamber, a heart valve holder, and a valve connected to a timer. In each embodiment, the components are combined in a fluid circuit to create a variable cycling and pulsatile fluid flow for seeding and culturing which can closely resemble the physiological conditions found in the human heart.

27 Claims, 9 Drawing Sheets

APPARATUS AND METHOD FOR STERILIZING, SEEDING, CULTURING, STORING, SHIPPING, AND TESTING TISSUE, SYNTHETIC, OR MECHANICAL HEART VALVES ORVALVE SEGMENTS

BACKGROUND OF THE INVENTION

1. Technical Field

The present invention relates to the sterilization, seeding, culturing, storing, shipping, and testing of heart valves. Specifically, the present invention relates to an apparatus and method for sterilizing heart valves and then seeding and culturing the heart valves with human cells, resulting in valves populated with viable human cells capable of displaying the durability and functionality of a healthy human heart valve.

2. Discussion of the Related Art

Biological heart valve implants are steadily increasing in importance. In the past, biological heart valve implants, typically porcine or bovine in origin, were fixed with glutaraldehyde prior to implantation so as to render the original biological tissue inert with respect to the living host environment and to bring about stabilization of the tissue so that it has a fixed configuration. However, glutaraldehyde-treated valves do not allow for infiltration and colonization by the host cells, which is essential to remodeling and tissue maintenance. Consequently, these glutaraldehyde-treated valves degrade with time and will eventually malfunction.

More recently, tissue-engineered heart valves are being developed which have been sterilized and then seeded and cultured, in vitro, with cells. These xenogeneic biological valves may be superior to glutaraldehyde-treated valves for use in replacement therapy in that they more closely display the durability and functionality of healthy human heart valves.

Historically, the seeding and culturing of tissue has taken place in a static environment such as a Petri or culture dish. However, there are disadvantages to seeding and culturing tissue in such an environment. For example, the lack of circulation of nutrients in these static systems results in a slow and ineffective seeding and culturing process. Moreover, cells which are seeded and cultured in a dynamic environment are more likely to tolerate the physiological conditions which exist in the human body once implanted. Thus, there is a need for a dynamic environment in which to seed and culture tissue-engineered heart valves and other prosthetic devices.

Non-static environments for treating heart valves are known in the related art. For example, U.S. Pat. No. 5,279,612 to Eberhardt discloses a method of glutaraldehyde treating porcine heart valves in which the glutaraldehyde fluid flow through the valve is alternated so as to cause the valve leaflets to fully open and close.

The use of non-static fluid flow across a valve has also been seen in the area of heart valve durability/fatigue testing. For example, U.S. Pat. No. 5,272,909 to Nguyen and U.S. Pat. No. 4,546,642 to Swanson disclose complex mechanical devices for testing the function of artificial or biological heart valves in which bidirectional fluid flow is utilized.

While the related art has included several devices for fixing and testing heart valves using bidirectional fluid flow, no dynamic devices for seeding and culturing heart valves exist. Moreover, the related art devices for fixing and testing heart valves have a number of disadvantages. These devices are mechanically complex, with many moving parts, and are thus expensive, prone to failure, and not adaptable to large scale use. More importantly, many of these devices do not closely approximate the cycling and pulsatile flow which is found in the human heart.

SUMMARY OF THE INVENTION

It is therefore an object of the invention to provide a dynamic environment for seeding, culturing, and testing heart valves which closely approximates the physiological conditions found in the human heart.

It is a further object of the invention to provide a less complex, precise mechanical device with a minimum of moving parts to provide such an environment.

It is yet a further object of the invention to provide a 10 closed system free from contamination for sterilizing, seeding, culturing, storing, shipping, and testing heart valves.

In accordance with the present invention, there is provided an apparatus and method for sterilizing, seeding, culturing, storing, shipping, and testing heart valves.

Specifically, the present invention is an apparatus and method for seeding and culturing heart valves with human cells, resulting in a heart valve populated with viable human cells.

The apparatus according to a preferred embodiment of the invention comprises a fluid reservoir, an elastomeric bladder, an alternating pressure source, and a heart valve holder. By varying pressure to the bladder, the pressure differential across the heart valve secured within the valve holder is altered, and a variable cycling and pulsatile fluid flow resembling that found in the human heart may be achieved.

In an alternative embodiment of the present invention, the apparatus comprises a fluid reservoir, a pump, a venturi tube, a heart valve chamber, and a pincher valve connected to a timer. By adjusting the rate at which the pincher valve is opened and closed, the pressure differential across the heart valve is altered as in the preferred embodiment so that a variable cycling and pulsatile fluid flow is generated. In this manner, the invention advantageously utilizes a mechanically non-complex apparatus to create a dynamic environment in which to seed and culture tissue-engineered heart valves.

BRIEF DESCRIPTION OF THE DRAWINGS

These and other features, aspects and advantages of the present invention will become more readily apparent from the following detailed description, which should be read in conjunction with the accompanying drawings in which:

FIGS. 2A–2B illustrate the operation of a bladder according to the invention, wherein FIG. 2A illustrates the bladder in an inflated state and FIG. 2B illustrates the bladder in a deflated state;

FIGS. 4A–4C illustrate an exemplary embodiment of a valve holder according to the invention, wherein FIG. 4A is a side view, FIG. 4B is a top view, and FIG. 4C is a cross-sectional view through line C—C of FIG. 4B;

FIGS. 7A–7C illustrate yet another alternative exemplary embodiment of a valve holder, wherein FIG. 7A is a top view, FIG. 7B is a cross-sectional view through line B—B of FIG. 7A, and FIG. 7C is a side view;

FIGS. 8A–8B illustrate an exemplary embodiment of a treatment chamber according to the invention, wherein FIG. 8A is a top view and FIG. 8B is a cross-sectional view through line B—B of FIG. 8A; and FIGS. 9A–9B illustrate an alternative exemplary embodiment of a treatment chamber, wherein FIG. 9A is a top view and FIG. 9B is a cross-sectional view through line B—B of FIG. 9A.

DETAILED DESCRIPTION OF THE INVENTION

Figure 1:
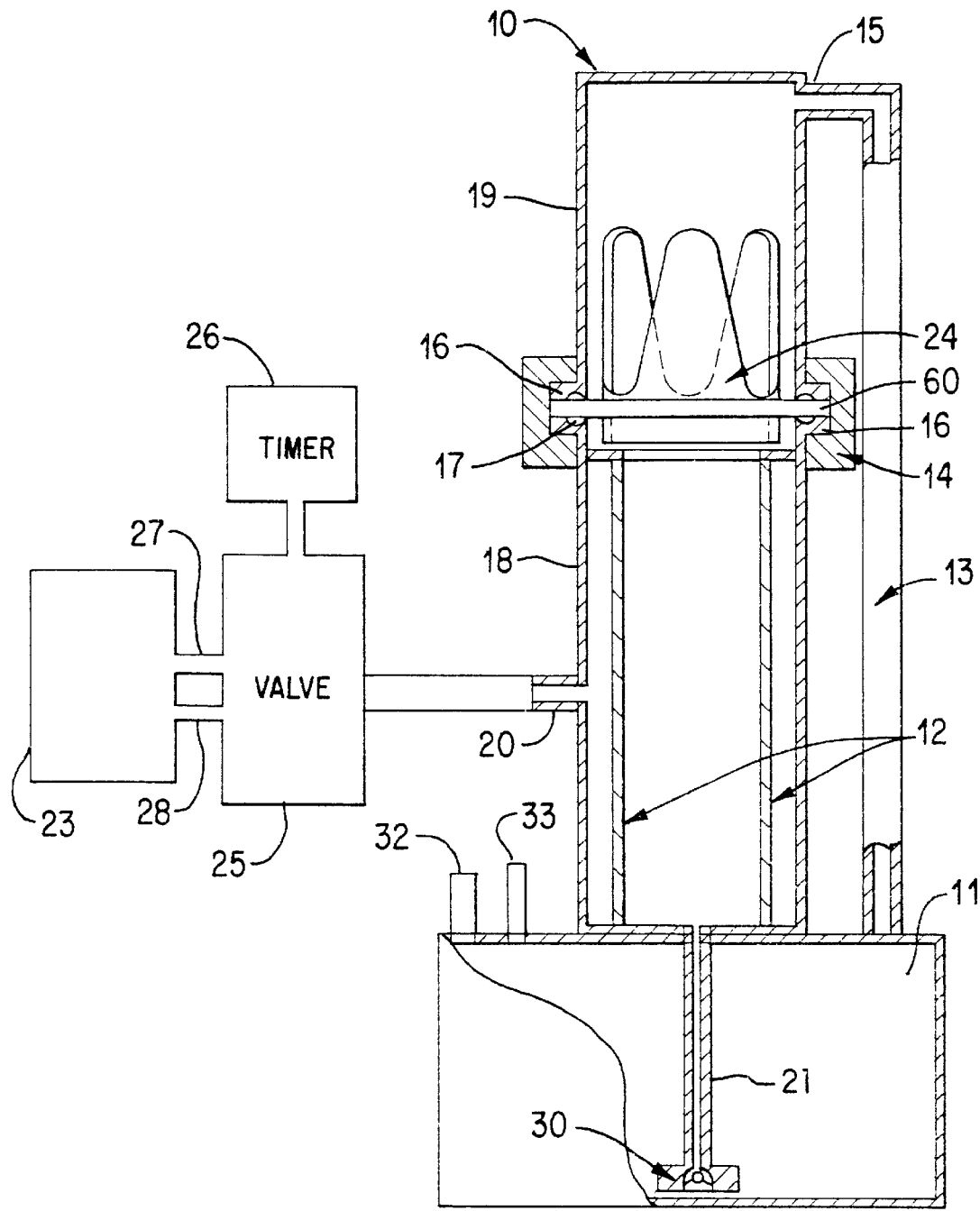
FIG. 1 illustrates an apparatus according to the present invention for sterilizing, seeding, culturing, storing, shipping, and testing a prosthesis.

The following embodiments of the present invention will be described in the context of an apparatus and method for sterilizing, seeding, culturing, storing, shipping, and testing heart valves, although those skilled in the art will recognize that the disclosed methods and structures are readily adaptable for broader application. Note that whenever the same reference numeral is repeated with respect to different figures, it refers to the corresponding structure in each such figure.

FIG. 1 discloses a system for sterilizing, seeding, culturing, storing, shipping, and testing heart valves.

According to a preferred embodiment of the invention, this system primarily comprises a valve bioreactor 10, an alternating pressure source 23, a valve 25, and a timer 26.

Bioreactor 10 contains a fluid reservoir 11 for storing fluid for the system. Examples of fluid which may be used in the system include, but are not limited to, sterilizing fluid, tanning fluid, fluid containing cells, or fluid containing a culture medium. It is to be understood that during testing, seeding, and culturing in a preferred embodiment, the fluid may be advantageously kept at human body temperature, and may be composed of a fluid which approximates the viscosity of human blood. One illustrative example of a solution which approximates the viscosity of blood is saline with glycerol. In a preferred embodiment, fluid reservoir 11 may include an aspiration port 33 for removing or replenishing the fluid contained in the system.

During use, the fluid contained in reservoir 11 is retrieved through check valve 30 and fluid line 21 by the action of pneumatic pressure chamber 18 and bladder 12, which may be comprised of any suitable elastomeric material. An illustrative suitable bladder is the Cutter/Miles double-valved hand activated blood pump. Bladder 12, which is contained in chamber 18, forces fluid from reservoir 11 through a heart valve mounted on valve holder 24 (valve holder 24 is described in detail in conjunction with FIGS. 4–7 below) by being alternately compressed and expanded by alternating pressure source 23 in conjunction with valve 25 and timer 26. The compression and decompression of bladder 12 is discussed in detail below in conjunction with FIGS. 2A–2B. Alternating pressure source 23 preferably may be any standard pump capable of providing both positive pressure and negative (or vacuum) pressure, such as a piston or diaphragm pump. Valve 25 accepts the positive pressure and negative pressure from pump 23 through lines 27 and 28, respectively. Due to signals from timer 26, valve 25 causes alternating positive and negative pressure to be applied to bladder 12 from line 20. Valve 25 may be any type of inline valve capable of directing and regulating multiple lines. One such valve is the MAC 45S, model 45A-AA1-DAAA-1BA.

Figure 2A:
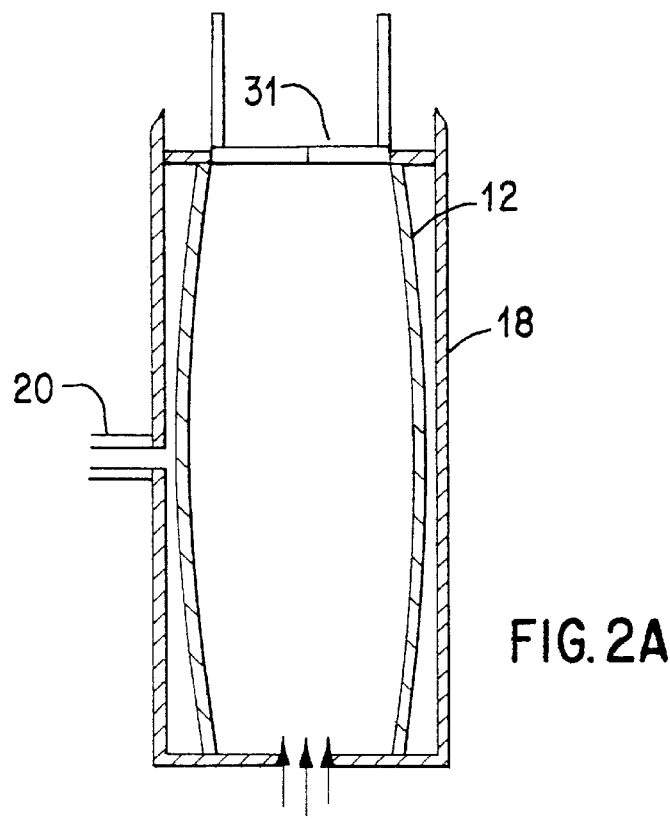
Figure 2B:
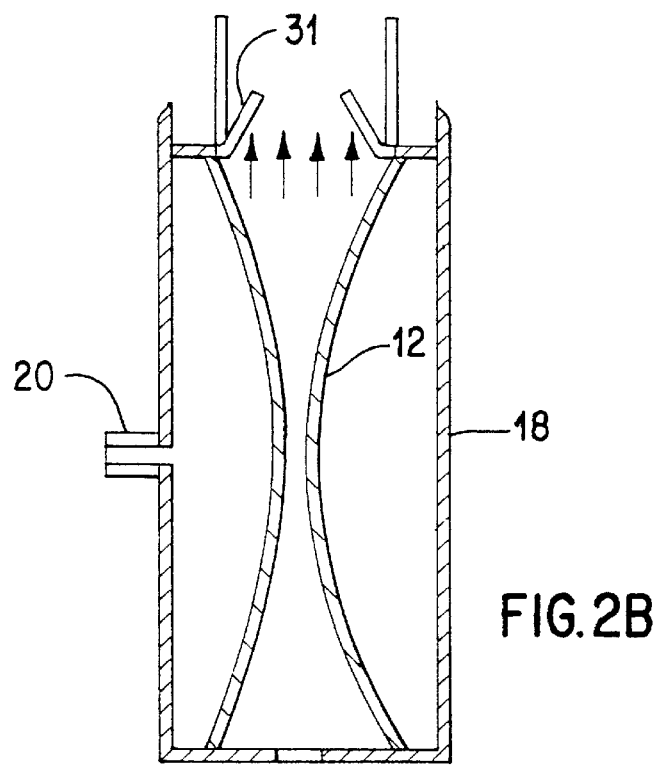

FIGS. 2A and 2B particularly point out and illustrate the movement of bladder 12 during use. FIG. 2A shows bladder 12 when a negative pressure is applied from line 20. When negative pressure is applied, fluid will be drawn from fluid reservoir 11 (as shown by the arrows) until bladder 12 is filled with fluid and is in a fully expanded state. Note that while fluid is being drawn from reservoir 11, the valve leaflets (shown as barrier 31 in FIG. 2A) of the heart valve contained in valve holder 24 (not shown in FIG. 2A) are forced closed, thus ensuring that no fluid enters the bladder from above.

Once the signal from timer 26 causes a positive pressure to be applied to bladder 12, the fluid contained in the bladder is forced through the heart valve as shown by the arrows in FIG. 2B, thus causing the valve leaflets to fully open. Note that during the compression of bladder 12 no fluid reenters the bladder due to the action of check valve 30 (shown in FIG. 1). However fluid does recirculate through return line 13 to media reservoir 11. In this manner, a cycling and pulsatile fluid flow through the heart valve may be generated.

As shown in FIG. 1, once the fluid is forced through the heart valve, the fluid exits chamber 19 through outlet 15 and is returned to reservoir 11 through return line 13. Return line 13 may be made of any type of medical grade tubing suitable for transporting fluid. Return line 13 may be made of a substance which allows for the diffusion of gas. This is beneficial because human cells placed in the system need a minimum concentration of carbon dioxide to survive. Return line 13 may also be made longer than necessary for fluid connection purposes so as to allow for a higher gas diffusion rate by providing more surface area. However, in a preferred embodiment of the invention, return line 13 is made of a noncompliant substance such as polyurethane which can withstand pressure within the system.

A gas port 32 supplying the appropriate mixture of gas may also be connected to the apparatus to provide a direct source of gas to the system. If gas port 32 is connected to the system, a one way filter can be placed at the connection between gas port 32 and the apparatus to eliminate any airborne contaminants.

Chambers 18 and 19, as well as fluid reservoir 11, of bioreactor 10 may be composed of any rigid, bio-compatible material capable of being sterilized such as Teflon, PVC, polycarbonate, or stainless steel. It is to be further understood that chambers 18 and 19 also contain ferrules or flanges 16 which allow the chambers to be secured together by clamp 14. Clamp 14 may be any suitable clamp such as a sanitary clamp. Alternatively, chambers 18 and 19 may be threaded together as shown in FIG. 8B below. The connection between chambers 18 and 19 when using the flange design (FIG. 1) may be made leak-proof by a gasket or an o-ring, which can be seated in the annular grooves 17 of flanges 16, found in each chamber. As is also shown in FIG. 1, flange 60 of valve holder 24 can be made to fit securely in between chambers 18 and 19 so as to also form a leak-proof seal. In addition, chamber 19 may be sealed at outlet 15 as well as at a point between valve holder 24 and bladder 12 by known means so as to form a sealed chamber. As will be discussed in detail below, sealed chamber 19 may be used to sterilize, store, and ship heart valves.

Figure 3:
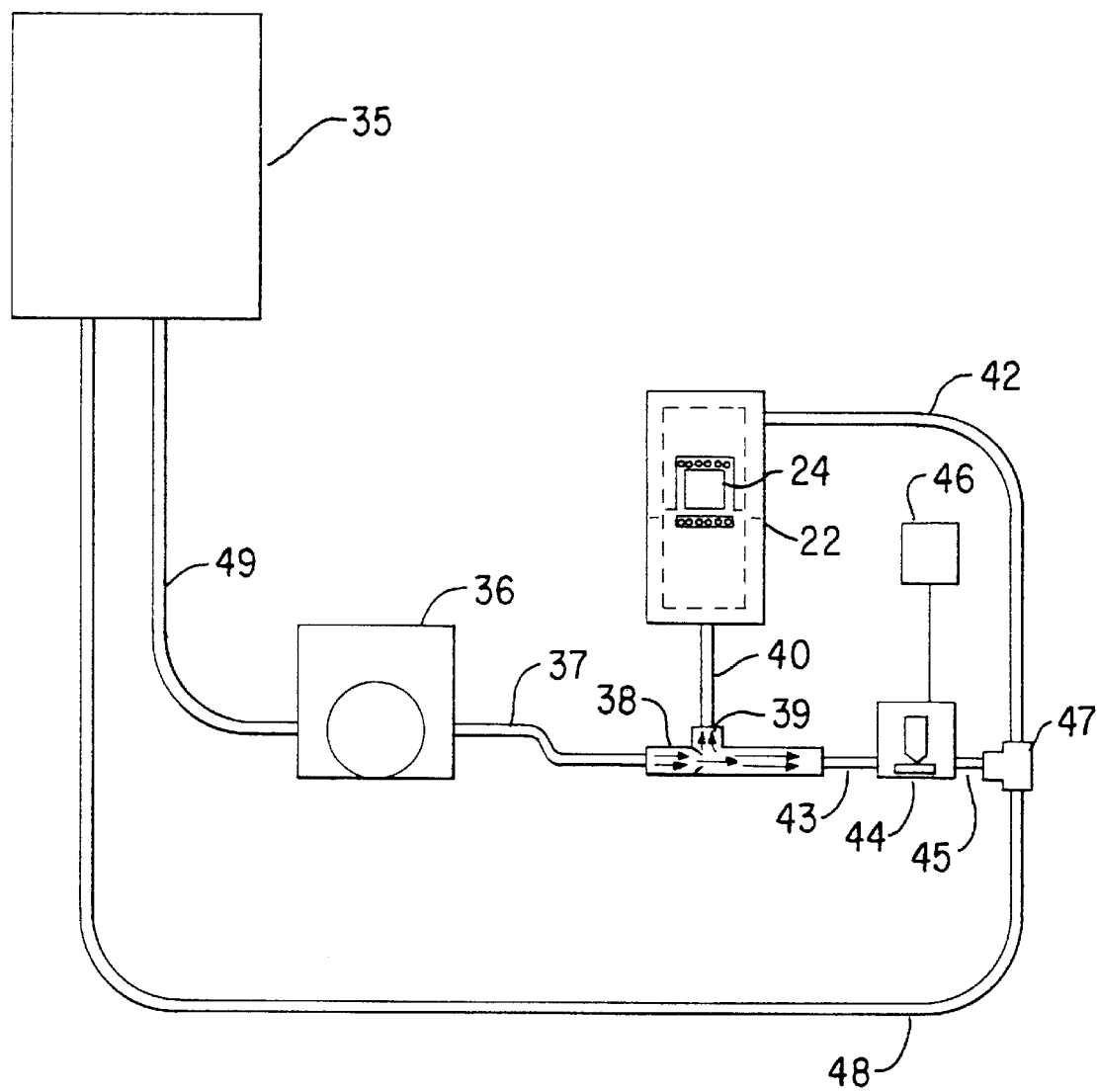
FIG. 3 illustrates an alternative exemplary embodiment of an apparatus according to the present invention for sterilizing, seeding, culturing, storing, shipping, and testing a prosthesis.

FIG. 3 discloses an alternative system for sterilizing, seeding, culturing, storing, shipping, and testing heart valves. According to this embodiment of the invention, the system primarily comprises a fluid reservoir 35, a pump 36, a venturi tube 38, a treatment chamber 22, and a pincher valve 44 connected to a timer 46.

Fluid reservoir 35, like fluid reservoir 11 in FIG. 1, is used to store fluid for the system (two illustrative suitable reservoirs would be the Gibco-BRL 1L media bag and any type of rigid, sterilizable container). Examples of fluid which may be used in the system are the same as those discussed in detail in conjunction with FIG. 1 above. In FIG. 3, the fluid contained in reservoir 35 is retrieved through fluid line 49 by pump 36. Fluid line 49, as well as all other fluid lines in the system, may be made of any type of medical grade tubing suitable for transporting the fluid in use. However, the fluid lines may preferably be made of a substance such as silicone which allows for the diffusion of gas. Pump 36 may be preferably any fluid pump which can achieve the flow rate found in the human heart. One such pump is the Masterflex L/S Digital Drive peristaltic pump manufactured by Cole-Palmer, although one skilled in the art could select from a variety of commercially available pumps. Pump 36 propels the fluid from reservoir 35 to venturi tube 38 through fluid line 37.

Venturi tube 38 may be any type of constriction mechanism which causes a drop in pressure as fluid flows through it. Side port 39 is located in the side of the venturi tube, immediately downstream from the constriction. The drop in pressure through venturi tube 38 is used to draw fluid from fluid line 40 through side port 39 and into the flow stream from fluid line 37 to fluid line 43. One illustrative example of a suitable venturi tube is the Nalgene Vacuum Pump with a maximum vacuum of 28.5 in.Hg. Through use of venturi tube 38, and as further discussed below, cycling and pulsatile bi-directional fluid flow through treatment chamber 22 may be achieved.

Fluid flows from venturi tube 38 to pincher valve 44 through fluid line 43. Pincher valve 44 is connected to timer 46 which may be used to variably open and close pincher valve 44. Pincher valve 44 may be any type of valve which can be variably opened and closed according to a desired program. (e.g., the Solenoid Valve manufactured by Bio-Chem Valve Corp).

Treatment chamber 22 is connected to side port 39 of venturi tube 38 by fluid line 40. Treatment chamber 22 houses valve holder 24, which in turn holds the heart valve firmly in place within the chamber. Exemplary embodiments of valve holder 24 are shown in more detail in FIGS. 2–5, as are embodiments of treatment chamber 22 in FIGS. 6–7.

The outlet of chamber 22 and the outlet of pincher valve 44 are connected to line tee 47 by fluid lines 42 and 45, respectively. Line tee 47 connects the system back to fluid reservoir 35 through fluid line 48.

By connecting the system in this manner, a variable cycling and pulsatile flow may be achieved through treatment chamber 22. Specifically, when pincher valve 44 is closed due to signals from timer 46, fluid flows into venturi tube 38, out the side port 39, and through treatment chamber 22 from fluid line 40 to fluid line 42. However, when pincher valve 44 is opened due to signals from timer 46, venturi tube 38 draws fluid into side port 39 from treatment chamber 22, causing fluid to flow in a direction from fluid line 42 to fluid line 40. Thus, by altering the pressure differential across the heart valve, a variable cycling and pulsatile fluid flow closely resembling the physiological conditions of the human heart may be advantageously achieved in the system.

Figure 4A:
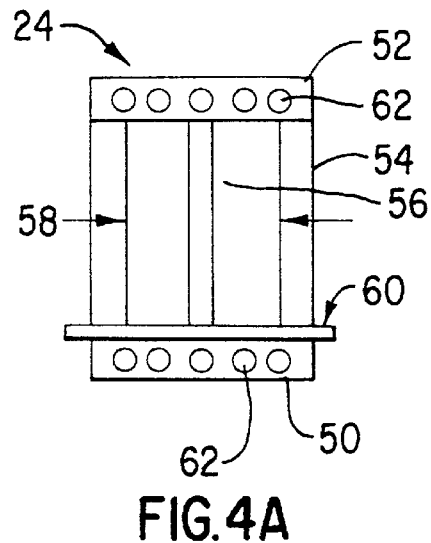
Figure 4B:
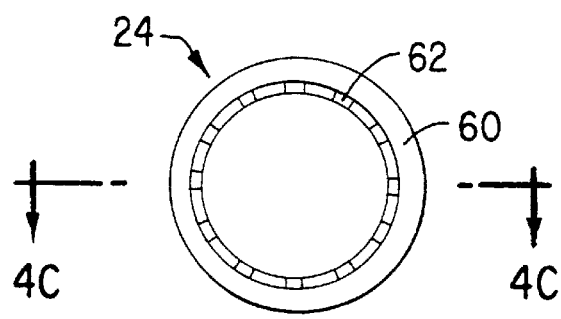
Figure 4C:
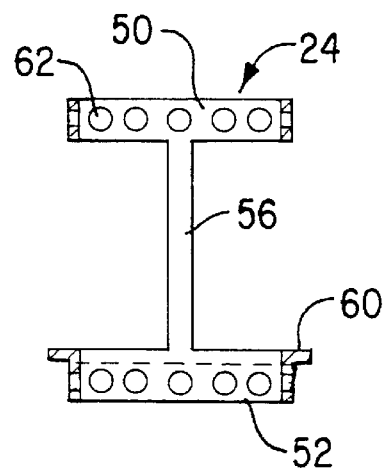

As shown in more detail in FIGS. 4A–4C, valve holder 24 includes inlet ring 50 connected to outlet ring 52 by three struts 54, 56, and 58. Each ring 50 and 52 contains a plurality of evenly spaced holes 62. Valve holder 24 also includes a flange 60 above inlet ring 50. A heart valve may be secured in valve holder 24 by a variety of means, including sutures, c-clips, or surgical staples. These securing means are placed through holes 62 of inlet ring 50 and outlet ring 52 so as to firmly secure the heart valve to valve holder 24.

The combination of struts 54, 56, and 58, inlet ring 50 and outlet ring 52 advantageously exposes a majority of the exterior surface of the secured heart valve to the fluid media so as to facilitate the seeding and culturing process. However, it is to be understood that more struts may connect rings 50 and 52 so as to increase the rigidity and stability of the structure and to decrease the surface area of the heart valve that is exposed to the fluid in the system.

Figure 5:
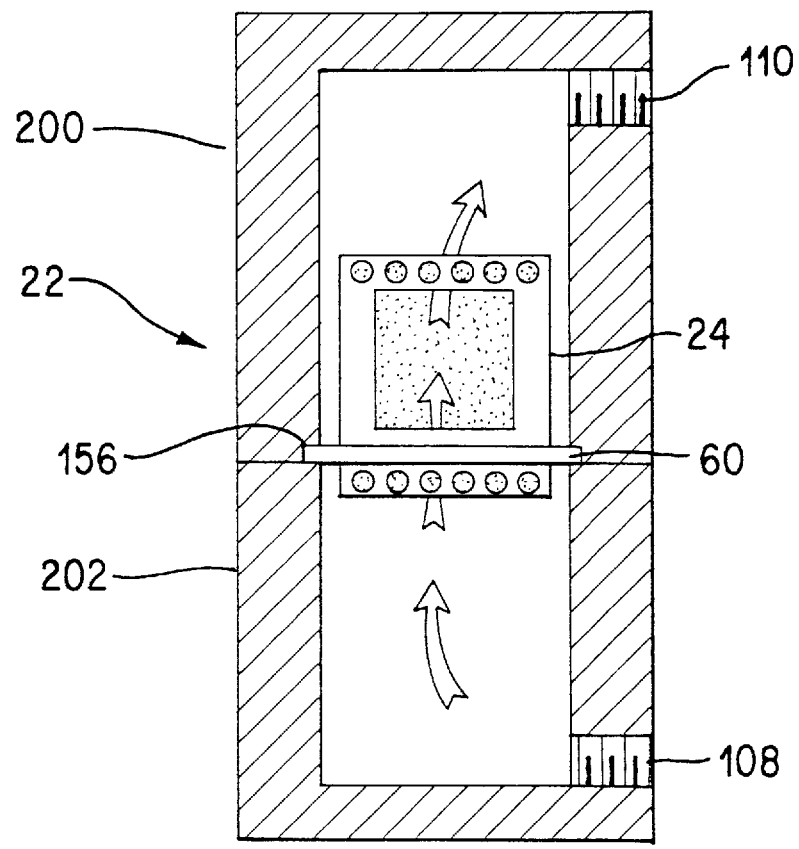
FIG. 5 illustrates a treatment chamber containing a valve holder and a heart valve according to one embodiment of the invention.

FIG. 5 shows treatment chamber 22 containing valve holder 24 and a heart valve (shown as the shaded region in valve holder 24). Flange 60 of valve holder 24 can be made to fit securely within groove 156 so as to form a seal within treatment chamber 22 at the joining of the hollow chambers 200 and 202. Securing valve holder 24 within chamber 22 in this manner advantageously assures that not only will the fluid media entering inlet flow 108 pass through (as shown by the arrows) and not around the heart valve attached to valve holder 24, but that it will also make contact with the exterior of the heart valve due to flow being permitted around the valve holder in chamber 200 and thus, between the struts of the valve holder.

Figure 6:
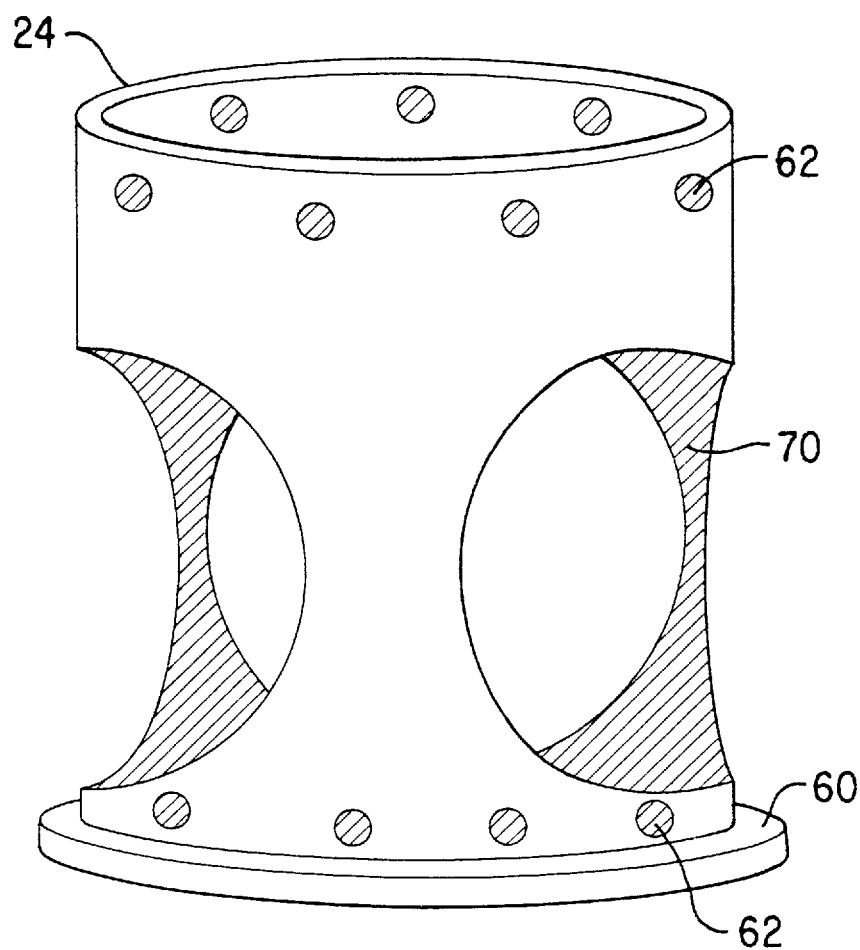
FIG. 6 illustrates an alternative exemplary embodiment of a valve holder.

FIG. 6 illustrates an alternative exemplary embodiment of valve holder 24. In this embodiment, valve holder 24 is a substantially solid cylinder with three evenly spaced circular openings 70. Circular openings 70 allow the heart valve sinuses to resume their natural, expanded shape while the heart valve is attached to valve holder 24. As in the first embodiment of valve holder 24, a heart valve may be attached to valve holder 24 by a variety of means including sutures or surgical staples. These securing means may be placed through holes 62 in both the inlet and outlet ports of valve holder 24 so as to firmly secure the heart valve to the valve holder.

Figure 7A:
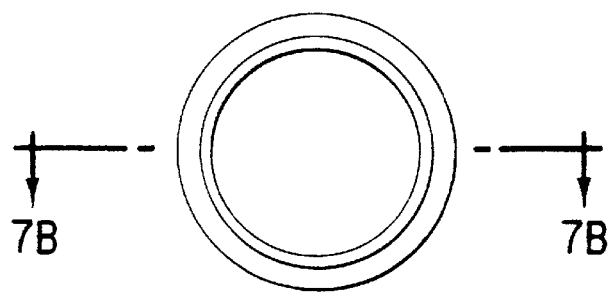
Figure 7B:
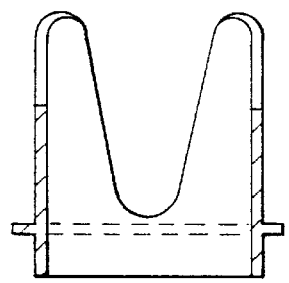
Figure 7C:
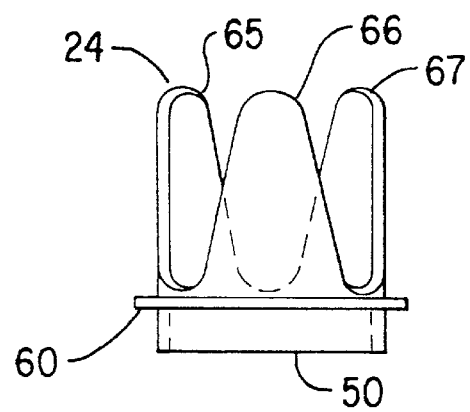

FIGS. 7A–7C illustrate the preferred embodiment of valve holder 24. In this embodiment, valve holder 24 includes inlet ring 50 and flange 60. Connected to inlet ring 50 are three commissures 65, 66, and 67 which are shaped substantially like a biological valve which has been prepared for implantation. Commissures 65, 66, and 67 act as supports for valves attached to valve holder 24. Like the above embodiments, inlet ring 50 and commissures 65, 66, and 67 may include holes so as to aid in the connection of the heart valve to valve holder 24 with the above mentioned securing means.

In still another alternative embodiment, valve holder 24 may comprise a solid cylinder so that the exterior surface of the heart valve secured to valve holder 24 is not exposed to any fluid media.

Finally, it is to be understood that valve holder 24 may be composed of any bio-compatible, rigid or compliant material capable of being sterilized, such as Delrin, Teflon, polycarbonate, stainless steel, silicone, polyurethane, or rubber. If valve holder 24 is composed of a compliant material, then connecting holes are unnecessary in the above embodiments of valve holder 24, as the securing means such as sutures, c-clips, or surgical staples may be punched through the compliant material. Alternatively, valve holder 24 may be composed of a material resembling mesh or screen so as to maximize the surface area of the heart valve which is exposed to the fluid media.

Figure 8A:
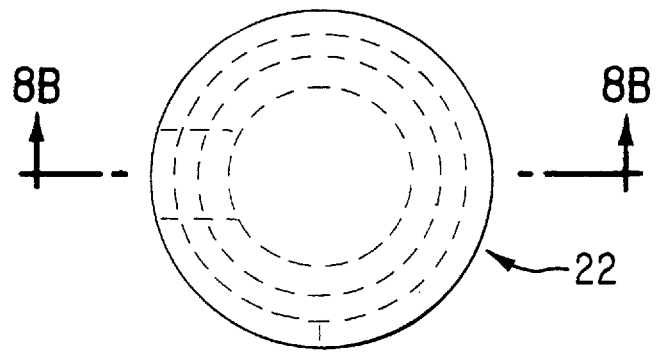
Figure 8B:
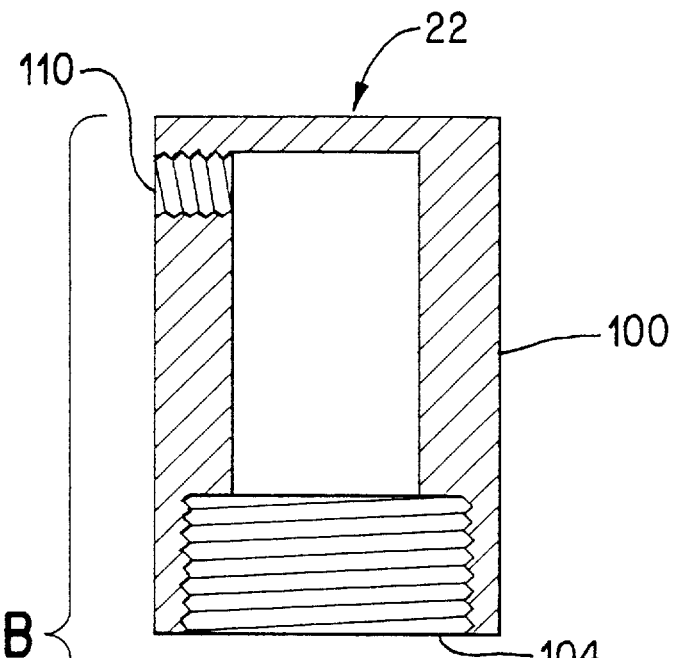
Figure 8B:
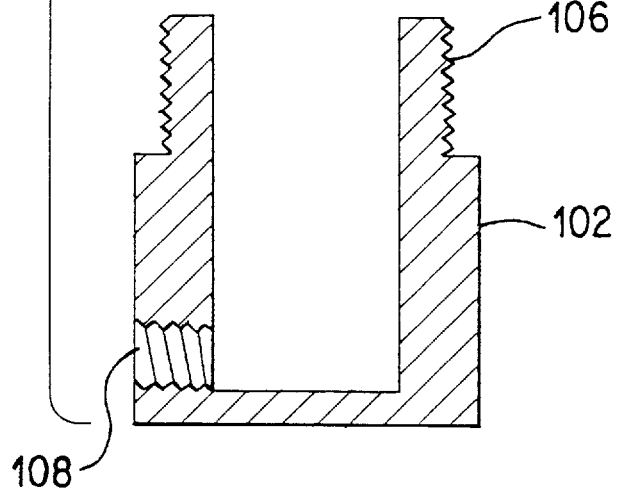

FIGS. 8A–8B show an alternative embodiment of treatment chamber 22. Chamber 22 comprises two substantially hollow chambers 100 and 102 which are preferably cylindrical, with one end sealed. Chambers 100 and 102 are fastened through the use of inner threads 104 and outer threads 106. The connection between chambers 100 and 102 may be made leak-proof by the use of a gasket or o-ring. Inlet port 108 at the bottom of treatment chamber 22 and outlet port 110 at the top of the chamber allows for the perfusion and/or circulation of fluid into and through the chamber. As shown in FIG. 3, outlet port 110 is used to attach treatment chamber 22 to fluid line 42 while inlet port 108 is used to attach the chamber to fluid line 40. Treatment chamber 22 preferably may be composed of any biocompatible material which is leak-proof, such as Delrin, Teflon, polycarbonate, PVC, or stainless steel.

It is to be understood that in order to view heart valves or other protheses within treatment chamber 22, a viewing port may be placed at any point on the chamber, or alternatively, chamber 22 may be made of an optically clear material such as polycarbonate or PVC.

It is to be further understood that inlet port 108 and outlet port 110 of valve chamber 22 may be sealed in a known manner (e.g., lure locks or threaded plugs) so as to create a sealed chamber 22 free from contamination. Sealed treatment chamber 22, as well as sealed chamber 19 discussed in conjunction with FIG. 1 above, may be used to sterilize, store, and ship heart valves or other protheses. In particular, prior to placing the sealed treatment chamber 22 or chamber 19 into the system of FIGS. 1 and 3, a heart valve which is secured within the sealed chambers may be sterilized by chemical methods such as ethylene oxide or peracetic acid, radiation methods such as an electron beam or gamma rays, or steam sterilization. The sealed treatment chambers, containing the sterilized heart valve may then be placed back into the systems of FIGS. 1 and 3 for seeding and culturing and unsealed without contaminating the system or the heart valve.

Seeding and culturing of the heart valve in chambers 19 and 22 is generally accomplished by known techniques, with the added benefits and advantages gained from the cycling and pulsatile fluid flow achievable with the systems according to the present invention. Examples of suitable seeding and culturing methods for the growth of three-dimensional cell cultures are disclosed in U.S. Pat. No. 5,266,480, which is incorporated herein by reference. The techniques described in U.S. Pat. No. 5,266,480 for establishing a three-dimensional matrix, inoculating the matrix with the desired cells, and maintaining the culture may be readily adapted by a person of ordinary skill in the art for use with the present invention. more particularly U.S. patent application Ser. No. 08/488,165, entitled "Three Dimensional Human Cell Cultures on Cardiac Valve Frameworks and Their Use" and filed concurrently herewith by the assignee of the present application, teaches a method for culturing heart valves, which is also incorporated by reference herein.

Once the heart valve culture has reached the desired level of cell density, a preservative may then be pumped into chambers 19 and 22. Once chambers 19 and 22 are filled with the preservative, they may again be sealed so as to be used to store and/or ship the cultured and preserved heart valve. Preferably, the preservative is a cryo-preservative so that the valve may be frozen in the chambers. In this manner, sealed chambers 19 and 22 may be used to sterilize, culture, store, and ship heart valves or other protheses.

Figure 9A:
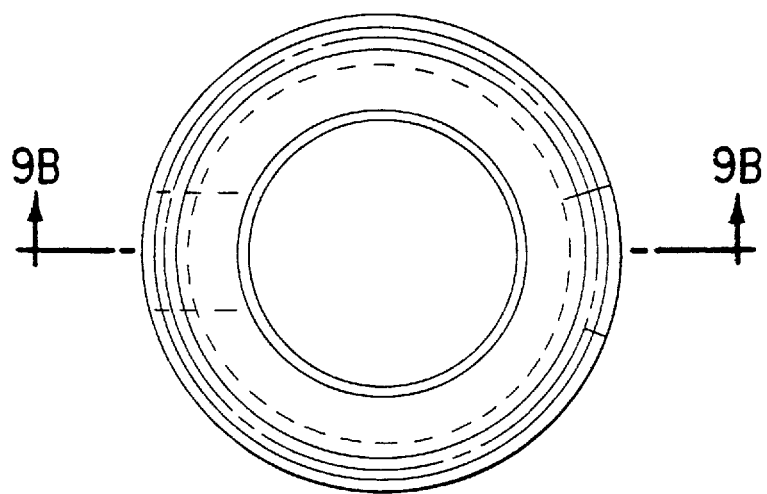
Figure 9B:
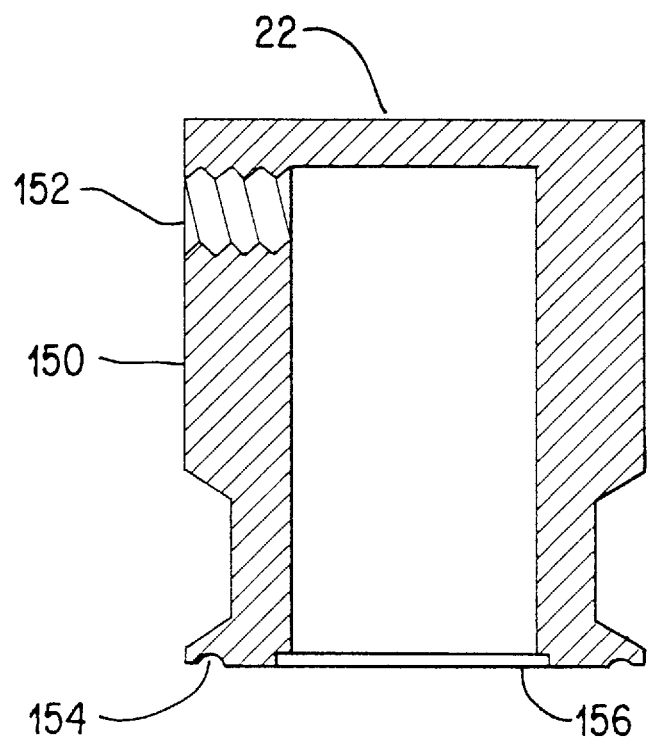

FIGS. 9A–9B illustrate an alternative preferred embodiment of treatment chamber 22. This alternative embodiment may also be composed of any inert, rigid material which is leak-proof. In this alternative embodiment, valve chamber 22 is composed of two substantially hollow chambers 150 which are cylindrical and have one end sealed. These chambers 150 are identical and may be connected by an apparatus such as a sanitary clamp or a union nut. The connection between hollow chambers 150 may be made leak-proof by a gasket or o-ring, which can be seated in annular groove 154 of the chambers 150. Chambers 150 contain an inlet or outlet port 152. Chambers 150 also contain hollowed out grooves 156, which may be used, as discussed in conjunction with FIG. 3, to hold valve holder 24 securely in place.

Various embodiments of the invention have been described. The descriptions are intended to be illustrative, not limitative. Thus, it will be apparent to those skilled in the art that modifications may be made to the invention as described without departing from the scope of the claims set out below.

We claim:

1. An apparatus, comprising:
   a housing defining a seeding and culturing chamber with first and second ports to permit flow of a medium therethrough;
   a heart valve substrate disposed within said chamber designed to facilitate three-dimensional tissue growth on said substrate;
   a heart valve substrate support structure mounted in the chamber, said structure supporting the heart valve substrate such that media flow between said ports is directed through the heart valve substrate and permitted to circulate around exterior surfaces of the heart valve substrate; and
   means for creating an alternating pressure differential across said heart valve substrate to provide alternating bidirectional flow acting on the heart valve substrate.

2. The apparatus of claim 1, wherein a portion of the support structure seals against the chamber housing to direct substantially all bidirectional flow through the heart valve substrate and a portion of the support structure is spaced away from the housing to permit media circulation around external surfaces of the heart valve substrate.

3. The apparatus of claim 1, wherein said means comprises a bladder moveable between a first position and a second position.

4. The apparatus of claim 3, wherein said bladder is disposed within a housing defining a chamber of alternating positive and negative pressure surrounding the bladder; and
   said bladder communicates with the seeding and culturing chamber and with a media supply, whereby negative pressure in the bladder chamber causes the bladder to expand and draw media from the seeding and culturing chamber and from the media supply and positive pressure in the bladder chamber causes the bladder to contract forcing media from the bladder into the seeding and culturing chamber.

5. The apparatus of claim 1, wherein said substrate comprises a three-dimensional framework having interstitial spaces bridgeable by cells.

6. The apparatus of claim 5, further comprising a three-dimensional tissue, said tissue comprising a plurality of cells attached to and substantially enveloping said framework.

7. An apparatus, comprising:

a varying pressure source;

a bladder cooperating with said varying pressure source, wherein said varying pressure source moves the bladder from a first position to a second position;

a supply of fluid in communication with the bladder;

chamber having a first port and a second port, said first port in communication with the bladder;

a heart valve substrate disposed within said chamber designed to facilitate three-dimensional tissue growth on said substrate; and a support structure mounted within the chamber, said support structure supporting the heart valve substrate within the chamber while permitting flow of the fluid around the heart valve substrate and in contact with the heart valve substrate;

wherein the bladder moving between said first and second positions creates an alternating pressure differential across the heart valve substrate to provide a bidirectional fluid flow acting on the heart valve substrate.

8. The apparatus of claim 7, wherein said chamber is defined by at least on wall; and said support structure defines a central opening through the support structure and is mounted in the chamber in sealing contact with said at least one wall such that fluid flow is forced through said central opening.

9. The apparatus of claim 8, wherein a portion of the support structure is spaced away from said at least one wall such that fluid is permitted to circulate around the support structure on at least one side of said sealing contact.

10. The apparatus of claim 9, wherein the heart valve substrate is securable within the support structure central opening and the support structure defines further opening to permit contact of said fluid permitted to circulate around the support structure with surfaces of the heart valve substrate.

11. The apparatus of claim 7, wherein a closed fluid connection is provided between the second port of the chamber and the fluid supply to provide a completely closed system.

12. The apparatus of claim 11, wherein said closed fluid connection between the second port of the chamber and the fluid supply allows for the diffusion of gas into the system.

13. The apparatus of claim 7, wherein said varying pressure source comprises a pump.

14. The apparatus of claim 7, further comprising:

a valve connected to a timer;

wherein said valve is connected in between said varying pressure source and said bladder and is controlled by said timer so as to alternatingly provide positive and negative pressure to said bladder from said varying pressure source, said positive and negative pressure moving said bladder between said first and second positions.

15. The apparatus of claim 7, wherein said substrate comprises a three-dimensional framework having interstitial spaces bridgeable by cells.

16. The apparatus of claim 15, further comprising a three-dimensional tissue, said tissue comprising a plurality of cells attached to and substantially enveloping, said framework.

17. A method for seeding and culturing a substrate, comprising:

exposing a substrate to a fluid media for seeding and culturing, said substrate designed to facilitate three-dimensional tissue growth on said substrate; and altering the pressure differential in said media across the substrate to provide alternating bidirectional flow acting on the substrate.

18. The method of claim 17, wherein said step of altering comprises:

creating a cycling pressure drop, in said fluid media to alternatingly provide a low pressure and a high pressure wherein the low pressure draws media across the substrate in a first direction and the high pressure forces media across the substrate in a second, opposite direction.

19. The method of claim 18, wherein said step of creating a cycling pressure drop comprises expanding and contracting a bladder between a first position and a second position to provide said low pressure and said high pressure across said substrate.

20. The method of claim 17, wherein said substrate is a heart valve substrate.

21. The method of claim 20, wherein said substrate comprises a three-dimensional framework having interstitial spaces bridgeable by cells.

22. A method for treating a prosthesis, comprising:

holding the prosthesis in a chamber adapted for flow of fluid therethrough from a fluid supply, said prosthesis designed to facilitate three-dimensional tissue growth on said prosthesis;

expanding a bladder to draw fluid into the bladder from the fluid supply and from the chamber through the prosthesis in a first direction; and contracting the bladder to force fluid from the bladder to act on the prosthesis in a second direction.

23. The method of claim 22, wherein the expanding and contracting of the bladder comprises creating a region of alternating positive and negative pressure surrounding the bladder.

24. The method of claim 22, further comprising:

recycling fluid from the chamber into the fluid supply; and introducing gas into the fluid during said recycling.

25. The method of claim 22, wherein the expanding and contracting bladder creates an alternating pressure differential across the prosthesis to provide a bidirectional flow through the prosthesis.

26. The method of claim 22, wherein the prosthesis is a heart valve prosthesis.

27. The method of claim 26, wherein said prosthesis comprises a three-dimensional framework having interstitial spaces bridgeable by cells.

* * * * *